United States Patent
Waranis et al.

(10) Patent No.: US 7,029,698 B2
(45) Date of Patent: Apr. 18, 2006

(54) ACETAMINOPHEN COMPOSITIONS

(75) Inventors: Robert Waranis, Annandale, NJ (US); Durwin O. Fontenette, Brandon, FL (US)

(73) Assignee: R.P. Scherer Technologies, Inc., Las Vegas, NV (US)

( * ) Notice: Subject to any disclaimer, the term of this patent is extended or adjusted under 35 U.S.C. 154(b) by 102 days.

(21) Appl. No.: 09/990,497

(22) Filed: Nov. 21, 2001

(65) Prior Publication Data

US 2003/0096872 A1    May 22, 2003

(51) Int. Cl.
*A61K 9/48*    (2006.01)
*A61K 9/64*    (2006.01)

(52) U.S. Cl. .................. 424/451; 424/454; 424/456

(58) Field of Classification Search ................ 424/400, 424/454, 456, 451
See application file for complete search history.

(56) References Cited

U.S. PATENT DOCUMENTS

| | | | |
|---|---|---|---|
| 3,956,490 A | 5/1976 | Higuchi et al. | 424/233 |
| 4,505,928 A | 3/1985 | Amundsen et al. | 514/492 |
| 4,786,725 A | 11/1988 | Amundsen et al. | 536/121 |
| 5,071,643 A * | 12/1991 | Yu et al. | 514/570 |
| 5,505,961 A * | 4/1996 | Shelley et al. | 424/451 |
| 5,529,923 A * | 6/1996 | Honour et al. | 435/252.1 |
| 5,735,105 A | 4/1998 | Stroud et al. | 53/411 |
| 6,020,007 A * | 2/2000 | Veech | 424/677 |
| 6,160,020 A | 12/2000 | Ohannesian et al. | 514/629 |

\* cited by examiner

*Primary Examiner*—Thurman K. Page
*Assistant Examiner*—Sharon Howard
(74) *Attorney, Agent, or Firm*—Andrew G. Rozycki; Donald O. Nickey

(57) ABSTRACT

The invention herein provides for an oral pharmaceutical composition adapted for use in capsular dosage forms comprising acetaminophen and a lactate salt alone or in combination with an acetate salt. Compositions of the invention exhibit improved solubility characteristics of the active ingredient per given fill volume, thereby permitting the use of smaller capsule sizes to deliver a given effective dose of the active ingredient. Compositions of the invention also exhibit improved clarity per concentration of active ingredient. The invention also provides for a capsular dosage form containing the composition.

15 Claims, No Drawings

ACETAMINOPHEN COMPOSITIONS

FIELD OF THE INVENTION

The present invention relates to pharmaceutical compositions comprising acetaminophen as the active ingredient. In particular, the invention pertains to acetaminophen compositions having improved solubility characteristics for encapsulation.

BACKGROUND OF THE INVENTION

Soft gelatin capsules or softgels are predominantly used to contain liquids wherein the active ingredients are present in the dissolved or suspended state. Filled one-piece softgels have been widely known and used for many years and for a variety of purposes. Because softgels have properties that are quite different from telescoping two-piece, hard shell capsules, the softgels are capable of retaining a liquid fill material. Softgels are often used to encapsulate consumable materials, including vitamins, dietary supplements, pharmaceuticals, and the like, in a liquid vehicle or carrier.

A particularly good bioavailability of a pharmacologically active substance is attained if the active substance is successfully dissolved in a suitable solvent and the encapsulated solution is administered to the patient. Producing highly concentrated solutions of any acidic, amphoteric or basic pharmaceutical compound is useful because it permits encapsulation in a softgel capsule of a unit dose which is small enough to permit easy swallowing. Filling a unit dose in a small softgel capsule to permit easy swallowing is useful because it increases patient acceptance of the medication. Patient acceptance of a medication is important because it is a substantial step towards solving the problem of patient noncompliance with the prescribed regimen.

Another utility of highly concentrated solutions is enhancement of bioavailability of the dissolved pharmaceutical compound or composition. Enhanced bioavailability occurs as a result of delivering the pharmaceutical already in solution at the site of absorption, thereby permitting faster and more uniform absorption to occur.

One problem associated with such compositions is that obtaining an appropriate solution of the pharmaceutical composition is sometimes difficult. Often it is not possible to dissolve the pharmaceutical compound in a volume of solvent small enough to produce a softgel which is appropriate in size from the standpoint of economics and patient acceptance. Furthermore, the solvent, carrier or vehicle itself must have sufficient solvating power to dissolve the desired amount of the pharmaceutical compound to produce a highly concentrated solution, while at the same time not hydrolyzing, dissolving or discoloring the capsule shell.

One approach to achieve this desired goal has been the use of enhanced solubility systems such as those described in Yu et al. U.S. Pat. No. 5,071,643. Yu et al. disclose soft gelatin capsules containing highly concentrated acetaminophen solutions comprising 25–40% by weight acetaminophen, hydroxide ions (e.g., potassium hydroxide), water, and polyethylene glycol. However, hydroxide ion sources at levels required to solubilize acetaminophen increase the pH of the solution to the extent that degradation of the softgel capsule occurs.

Other approaches to enhance the solubility of acetaminophen have been used as well. Shelley et al. U.S. Pat. No. 5,505,961 describes a method of increasing the solubility of acetaminophen alone or in combination with antihistamines, antitussives, desongestants, and expectorants to form clear solutions for encapsulation in softgel capsules. Shelley et al. teach compositions comprising acetaminophen, potassium or sodium acetate, polyethylene glycol and polyvinyl pyrrolidone which permits a 325 mg dose to be administered in the same size softgel as a 250 mg dosage product. The capsule sizes needed for a desired dose of these formulations, however, are still relatively large. Another drawback is that the acetate solvent system restricts the amount of other active compounds which can be used due to solubility limitations. Furthermore, the presence of acetate can adversely affect tolerance of certain analgesics.

There exists a need for improved softgel formulations containing pharmaceutical compounds such as acetaminophen which permit high concentrations of the drug to be solubilized in lower fill volumes thereby permitting the desired effective dose of drug to be administered to a patient using smaller capsule sizes.

SUMMARY OF THE INVENTION

The invention herein provides for an oral pharmaceutical composition for use in capsular dosage forms comprising acetaminophen and lactate salts alone or in combination with acetate salts which exhibit improved solubility characteristics of the active ingredient while at the same time permitting the use of smaller capsule sizes to deliver effective doses thereof. In a preferred composition, the combination of l-lactate (levos) and acetate salts are used in the composition. Furthermore, compositions have improved visual characteristics, e.g., clarity of appearance. The invention also provides for a capsular dosage form, such as a soft or hard gelatin capsule, containing such a composition.

Acetaminophen is difficult to dose in a solubilized form due to high therapeutic dose requirements (typically 500 to 1,000 mg) while still using a relatively small appropriate capsule size for patient compliance. It has been discovered that combinations of particular ingredients when used in conjunction with acetaminophen in a liquid fill composition, not only improve the solubility of the acetaminophen thereby permitting increased concentrations of the active ingredient for a given fill, but also improves the appearance of the fill composition as well by way of reduced observable crystallization. In particular, certain combinations of acetaminophen and solvent system comprising lactate salts alone, or both lactate salts and acetate salts, provide such improvements while at the same time provide formulations compatible with capsular encasing materials, such as gelatin.

In one aspect, the invention provides for a liquid oral pharmaceutical composition adapted for use in capsular dosage forms comprising acetaminophen as an active ingredient and a solvent system comprising an alkali metal lactate salt. Preferred alkali metal lactate salts are alkali metal l-lactate salts. Even more preferred as the alkali metal lactate salt is sodium l-lactate. The lactate salt can be used alone as the carboxylate salt, or preferably, together with an alkali metal acetate salt. When the combination is used, the preferred acetate salt is potassium acetate. The solvent system of the composition of the invention can further comprise polyethylene glycol and polyvinyl pyrrolidone.

Another aspect of the invention provides for a capsular dosage form containing a liquid pharmaceutical composition comprising acetaminophen as an active ingredient and a lactate salt, preferably a l-lactate salt. Suitable capsular dosage forms include, but are not limited to, capsule casings composed of gelatin, such as soft or hard gelatin.

One advantage of the invention is that concentrations of acetaminophen greater than about 40% by weight, and even about 42%, can be achieved per given volume, while still maintaining clarity of appearance of the composition. Furthermore, the composition is suitable for use in capsular materials subject to degradation, such as gelatin. For a given dosage size such as 325 mg, acetaminophen can be present in an amount of about 42% by weight of the fill composition. Accordingly, smaller capsule sizes and/or fewer capsules need to be used to deliver the same effective dose.

DETAILED DESCRIPTION OF THE INVENTION

As used herein, the general term "capsule" is intended to encompass any suitable one-piece capsular containment adapted for oral ingestion and which is adapted for use in conjunction with liquid fill compositions. The term includes capsules having casings composed of soft and hard materials, such as gelatin, starches, celluloses, hydrocolloids, gums, carageegans, or any other natural or synthetic material which can be used to encapsulate the liquid composition and be ingested by an animal. The term is intended to include a variety of capsule shapes and sizes, and is not intended to limit the dosage form to a specific type or shape.

The term "acetaminophen" as used herein is intended to include the chemical derivatives of the acetaminophen structure having equivalent pharmaceutical effect.

The invention generally includes a liquid oral pharmaceutical composition adapted for use in capsular dosage forms. Specifically, the capsular dosage forms suitable for use with the invention are those which are adapted to contain liquid fill compositions. A variety of capsule casing materials can be used in conjunction with the invention, providing they permit one-piece integrated molding manufacturing techniques. Examples of suitable casing materials include, but are not limited to, gelatin (soft and hard), starches, celluloses, carageegans, hydrocolloids, gums, and the like. Casing materials can be prepared using well-known and conventional techniques and materials readily available in the art.

The shape and size of capsules can vary in accordance with the invention. In addition to the conventional oblong shape, the capsules can be in the form of a sphere, oval, tablet, and the like. The size of the capsule used will vary in accordance to the volume of the fill composition intended to be contained therein.

The active ingredient of the composition of the invention is acetaminophen and chemical derivatives thereof having equivalent pharmaceutical effect. The amount of acetaminophen used in the pharmaceutical composition will depend upon the amount of the drug desired to be administered in the dosage form while maintaining the solubility and clarity characteristics of the entire composition including the solvent system.

The invention includes a solvent system for acetaminophen which comprises an alkali metal lactate salt. In particular, preferred for use in the solvent system of the invention are alkali metal l-lactate salts, such as sodium l-lactate. In preparing compositions of the invention, the solvent system to be used can contain the l-lactate salt alone or, preferably, in combination with an alkali metal acetate salt. When the acetate salt is used, potassium acetate is preferred. Surprisingly, it has been discovered that not only are the desirable properties of the fill composition obtained by virtue of the particular number of carbon atoms in the carboxylate chain used in the solvent system, but also are affected by the specific rotational chemistry of the carboxylate salt. In other words, not only are the best results obtained using lactate as compared to other carboxylate salts, but in particular l-lactate (levo) as compared to racemic dl-lactate salts. The highest concentrations of acetaminophen per given total fill volume can be obtained using l-lactate salt as the carboxylate salt. Alternatively and preferably, the concentration of acetaminophen per given fill volume can be increased even more when the combination of l-lactate and an acetate salt, such as potassium acetate, are used simultaneously.

The composition of the invention further includes within the solvent system polyethylene glycol (PEG) and polyvinylpyrrolidone (PVP). In a preferred embodiment, the polyethylene glycol is polyethylene glycol 600 (available from Union Carbide, Danbury, Conn.). Suitable polyvinylpyrrolidone includes Povidone 25 (available from BASF, Mount Olive, N.J. and ISP, Freetown, Mass.).

The amounts of each ingredient of the solvent system can vary slightly provided the solubility characteristics of acetaminophen and the desirable clarity of the overall fill composition are maintained. The lactate salt can generally be present in an amount ranging from about 4.0% to about 12.3% by weight of the fill composition. When present, the acetate salt can be present in an amount ranging from about 4.0% to about 7.0% by weight of the fill composition. When both l-lactate and acetate salts are used, the amount of l-lactate can be lower relative to the use of l-lactate alone in the solvent system. Polyethylene glycol can be present in an amount ranging from about 30.0% to about 40.0% by weight of the fill composition. Polyvinyl pyrrolidone can be present in an amount ranging from about 3.0% to about 7.0% by weight of the fill composition.

In the interest of minimizing the overall fill volume while maximizing the concentration of the active ingredient, the use of additional ingredients is possible but not recommended. The invention offers the advantage of making available the administration of a given dosage amount of active ingredient using smaller capsule sizes, thereby increasing patient comfort and compliance, as well as reduced packaging and materials volume. The clarity of the pharmaceutical fill composition provides a more appealing appearance and affords the ability to utilize visually appealing transparent capsule casing materials, as compared to compositions producing a cloudy or milky appearance.

Pharmaceutical compositions of the invention can be prepared generally using the basic preparation steps of initially solubilizing polyvinyl pyrrolidone in polyethylene glycol by mixing them together at a temperature of about 30° C. for approximately 15 to 20 minutes until the polyvinyl pyrrolidone is completely solubilized. The active ingredient, acetaminophen, can then be added to the mixture at high speed for a period ranging from about 30 minutes to about 45 minutes. During the addition step of acetaminophen, the temperature of the mixture can be slowly increased to about 65° C. and maintained. The carboxylate salts, i.e., lactate or lactate and acetate, and water can then be added. The temperature of the mixture can be increased to about 70° C. The mixture can be continuously stirred for a period ranging from about 1 hour to about 2 hours, while maintaining the temperature.

Conventional capsule manufacturing techniques and equipment can be used to prepare the composition-filled capsules of the invention. Typically, ribbon and die roller manufacturing techniques are suitable for preparation of the capsules of the invention. Encapsulation apparatuses such as that described in Stroud et al. U.S. Pat. No. 5,735,105, the entire text of which is incorporated by reference herein, can be used.

The following examples further illustrate aspects of the invention, and none of which are intended to be construed as limiting the invention.

EXAMPLES

Preparation of Acetaminophen Formulations:

A variety of formulations containing acetaminophen within different solvents and solvent compositions were compared. Each of the formulations was prepared by first mixing together polyethylene glycol (Polyethylene glycol 400 and 600) (available from Union Carbide, Danbury, Conn.) with polyvinyl pyrrolidone (Povidone 25 available from BASF, Mount Olive, N.J. and ISP, Freetown, Mass.) at 30° C. for approximately 15 to 20 minutes until the polyvinyl pyrrolidone (Povidone 25) was completely solubilized in the polyethylene glycol. Acetaminophen was added to the mixture at high speed for about 30 to 45 minutes, during which time the temperature of the mixture was slowly increased to 65° C. and maintained. The salts and water were then added, and the temperature of the mixture was increased to 70° C. The mixture was continuously stirred for 1 to 2 hours. Clarity and crystallization observation was done throughout the final steps of mixing.

Comparison of Acetaminophen Formulations (Lactate vs. Acetate Salts)

The following batch formulations were prepared in accordance with the above process:

| Formula | 1 (239-140A) | 2 (239-101) | 3 (239-102) | 4 (239-108) |
|---|---|---|---|---|
| | % by weight/grams per batch | | | |
| Polyethylene glycol 600 | 0.0%/0 | 38.8%/38.88 | 39.8%/39.82 | 35.3%/35.27 |
| Polyethylene glycol 400 | 36.3%/23.7 | 0.0%/0 | 0.0%/0 | 0.0%/0 |
| Povidone 25 | 3.8%/2.5 | 5.0%/5.0 | 5.0%/5.0 | 7.0%/7.0 |
| Acetaminophen | 39.9%/26.0 | 41.0%/41.0 | 41.0%/41.0 | 42.0%/42.0 |
| Sodium l-lactate | 12.3%/8.0 | 8.2%/8.2 | 0.0%/0 | 4.7%/4.675 |
| Potassium acetate | 0.0%/0 | 0.0%/0 | 7.2%/7.18 | 4.1%/4.089 |
| Water | 7.7%/5.0 | 7.0%/7.0 | 7.0%/7.0 | 7.0%/7.0 |
| Total | 100.0%/65.2 | 100.0%/100.1 | 100.0%/100.0 | 100.1%/100.3 |
| Total Fill Sample Volume 100.0 g = 83.3 ml | | | | |
| Clarity | Not clear | Cloudy | Cloudy | Clear |

As can be seen from the above data, the results show that the combined advantage of highest concentration of solubilized acetaminophen and clarity (indicating the observable presence or absence of crystallization) occurred with Formula 4, which contained the combination of sodium l-lactate and potassium acetate salts in the solvent system. Some crystallization occurred with the separate use of sodium l-lactate and potassium acetate, as seen from the results of Formulas 2 and 3. The combination of polyethylene glycol and only sodium l-lactate also resulted in crystallization.

Comparison of Acetaminophen Formulations Using Leverous vs. Racemic Lactate Salts:

Two acetaminophen-containing batch compositions were prepared according to the process described above, the ingredients and relative amounts being as follows:

| Formula | 5 (239-91A) | 6 (239-91B) |
|---|---|---|
| | % by weight/grams per batch | |
| Polyethylene glycol 400 | 36.3%/23.7 | 36.3%/23.7 |
| Povidone 25 | 3.8%/2.5 | 3.8%/2.5 |
| Acetaminophen | 39.9%/26 | 39.9%/26 |
| Sodium l-lactate | 12.3%/8.0 | 0.0%/0 |
| Sodium dl-lactate | 0.0%/0 | 12.3%/8.0 |
| Water | 7.7%/5.0 | 7.7%/5.0 |
| Total | 100.0%/65.2 | 100.0%/65.2 |
| Total Fill Sample Volume 100.0 g = 8.3 ml | | |
| Clarity | Clear | Hazy |

As can be seen from the above data, acetaminophen-containing formulations using l-lactate (leverous) exhibited clarity as compared to the dl-lactate (racemic) formulation. Observable crystallization occurred with the combination of acetaminophen and the racemic lactate salt, whereas the formulation using sodium l-lactate was clear.

Comparison of Acetaminophen Formulations Using Longer Chain Carboxylate Salts

The following batch formulations were prepared using the process described above.

| Formula | 7 (239-81) | 8 (239-85) | 9 (239-29) |
|---|---|---|---|
| | % by weight/grams per batch | | |
| Polyethylene glycol 600 | 41.9%/106.0 | 49.5%/120.0 | 42.9%/480.0 |
| Povidone 25 | 5.1%/13.0 | 5.2%/12.6 | 4.7%/52.9 |
| Acetaminophen | 32.1%/81.25 | 30.0%/72.7 | 29.1%/325.0 |
| Propylene glycol | 0.0%/0 | 0.0%/0 | 2.7%/30.0 |

-continued

| Formula | 7 (239-81) | 8 (239-85) | 9 (239-29) |
|---|---|---|---|
| Sodium propionate | 11.0%/28.0 | 0.0%/0 | 0.0%/0 |
| Sodium butyrate | 0.0% | 5.0%/12.0 | 0.0%/0 |
| Sodium benzoate | 0.0% | 0.0% | 7.3%/82.0 |
| Water | 9.9%/25.0 | 10.3%/25.0 | 13.2%/147.6 |
| Total | 100.0%/253.25 | 100.0%/242.3 | 99.9%/1117.5 |
| Total Fill Volume 100.0 g = 83.3 ml | | | |
| Clarity | Hazy | Clear/odor | Hazy |

Various formulations were prepared using longer chain carboxylate salts and results were observed. As can be seen, the formulations containing either sodium propionate or sodium benzoate and acetaminophen were hazy in appearance. Although the formulation containing sodium butyrate exhibited some clarity, an objectionable pungent odor was present. Furthermore, the concentration of acetaminophen was not significantly improved using the butyrate salt.

Other similar formulations using succinate, maleate and maleic acid were prepared. However, these formulations were not homogenous due to the lack of miscibility with polyethylene glycol.

As can be derived from the above results collectively, obtaining a collective balance between the desirable properties of increased solubility and avoiding crystallization while maintaining chemical compatibility amongst the various ingredients is surprisingly sensitive to relatively minor differences in the chemistry of the ingredients and their amounts. Even differences in the rotational nature of a compound (e.g., levo versus racemic salts) produce different results.

INDUSTRIAL APPLICABILITY

The compositions according to the invention permit the use of effective doses of acetaminophen to be prepared using smaller capsule sizes. This significantly reduces manufacturing costs and increases patient comfort. Furthermore, when transparent soft capsules are used for acetaminophen, the clarity and coloration of the inventive composition renders a more appealing final product.

The invention has been described with reference to specific ingredients, ranges, techniques, and the like. It will be understood to one of ordinary skill that reasonable modifications and variations of the same are possible without departing from the spirit or scope of the invention defined by the claims set forth hereinbelow.

What is claimed is:

1. An oral liquid pharmaceutical composition in a capsule comprising:
   acetaminophen as an active ingredient and a solvent system comprising a l-lactate salt.

2. The pharmaceutical composition of claim 1 wherein the l-lactate salt is sodium l-lactate.

3. The pharmaceutical composition of claim 1 wherein the solvent system of the composition further comprises an alkali metal acetate salt.

4. The pharmaceutical composition of claim 3 wherein the alkali metal acetate salt is potassium acetate.

5. The pharmaceutical composition of claim 1 wherein the solvent system further comprises polyethylene glycol and polyvinyl pyrrolidone.

6. An oral liquid pharmaceutical composition comprising:
   acetaminophen in an amount of at least about 40% by weight; sodium l-lactate in an amount of at least about 4.0% by weight; and potassium acetate in an amount of at least about 4.0% by weight.

7. The pharmaceutical composition of claim 6 wherein said acetaminophen is present in an amount of about 42% by weight.

8. A capsule containing an oral liquid pharmaceutical composition comprising:
   acetaminophen as an active ingredient and a solvent system comprising an alkali metal l-lactate salt.

9. The capsule of claim 8 wherein the l-lactate salt is sodium l-lactate.

10. The capsule of claim 8 wherein the solvent system further comprises an alkali metal acetate salt.

11. The capsule of claim 10 wherein the alkali metal acetate salt is potassium acetate.

12. The capsule of claim 8 wherein the solvent system of the composition further comprises polyethylene glycol and polyvinyl pyrrolidone.

13. The capsule dosage form of claim 8 wherein the composition comprises the following formula:
   acetaminophen in an amount of at least about 40% by weight;
   sodium l-lactate in an amount of at least about 4.0% by weight; and
   potassium acetate in an amount of at least about 4.0% by weight.

14. The capsule of claim 13 wherein acetaminophen is present in an amount of about 42% by weight.

15. The capsule of claim 8 wherein the capsular material comprises gelatin.

* * * * *